United States Patent [19]

Winter et al.

[11] Patent Number: 5,194,642

[45] Date of Patent: Mar. 16, 1993

[54] METALLO-ORGANIC PRECURSORS TO TITANIUM NITRIDE

[75] Inventors: Charles H. Winter, Grosse Pointe Park; Tilak S. Lewkebandara, Detroit; James W. Proscia, Dearborn; Philip H. Sheridan, Madison Heights, all of Mich.

[73] Assignee: Ford Motor Company, Dearborn, Mich.

[21] Appl. No.: 825,235

[22] Filed: Jan. 24, 1992

[51] Int. Cl.$^5$ .............................................. C07F 7/28
[52] U.S. Cl. ...................................................... 556/51
[58] Field of Search .......................................... 556/51

[56] References Cited

U.S. PATENT DOCUMENTS 4,535,000 8/1985 Gordon .............................. 427/160

OTHER PUBLICATIONS

Alcock et al., "catena-Di-μ-chloro-bis-μ-(trimethylsilylamino)-di[chlorotitanium(iv)]:Preparation, Properties, and Crystal Structure", Journal of the Chemical Society, Dalton Transactions, vol. 8, pp. 707-713 (1976).

Alastair J. Nielson, "Alkylimido Complexes of Titanium (IV)", Inorganica Chimica Acta, vol. 154, pp. 177-182 (1988).

Cotton et al., Advance Inorganic Chemistry: A Comprehensive Text, 4th Ed., Wiley-Interscience, New York, pp. 378-379 (1980).

Brown, G. M. and Maya, L., "Ammonolysis Products of the Dialkylamides of Titanium, Zirconium, and Niobium as Precursors to Metal Nitrides", Journal of the American Ceramic Society, v. 71 (1988) 78-82.

Seyferth, D. and Miganani, G., "The Preparation of Titanium Nitride and Titanium Carbonitride by the Preceramic Polymer Route" Gov. Rep. Announce. Index (US), v. 88 (1988) 827, 109.

Cowdell, R. T. and Fowles, G. W., "Amine Compounds of the Transition Metals. Part VI. The reaction of Titanium (IV) Cloride with Some Aliphatic Amines", Journal of the Chemical Society (1960) 2522-2566.

Primary Examiner—José G. Dees
Assistant Examiner—Porfirio Nazario
Attorney, Agent, or Firm—Charles H. Ellerbrock; Clifford L. Sadler

[57] ABSTRACT

A titanium tetrahalide is reacted with a primary alkyl or aryl amine to prepare a metallo-organic precursor, which thereafter may be volatilized to form a gaseous chemical vapor deposition precursor to titanium nitride, or may be pyrolyzed to form bulk titanium nitride.

13 Claims, No Drawings

METALLO-ORGANIC PRECURSORS TO TITANIUM NITRIDE

FIELD OF THE INVENTION

This invention relates generally to metallo-organic precursors to titanium nitride. More Particularly, the invention relates to novel metallo-organic precursors to titanium nitride which are useful for chemical vapor deposition and pyrolysis, and to their methods of preparation. This invention also contemplates novel processes for preparing titanium nitride by chemical vapor deposition and pyrolysis.

BACKGROUND OF THE INVENTION

Metallo-organic precursors have been used in recent years to prepare advanced materials such as titanium nitride, vanadium nitride, silicon carbide, silicon nitride, etc. These advanced materials advantageously have been deposited onto transparent glazings, e.g., glass, and other substrates by well-known coating processes such as, for example, atmospheric pressure chemical vapor deposition (APCVD), low pressure chemical vapor deposition (LPCVD), plasma enhanced chemical vapor deposition (PECVD), laser induced chemical vapor deposition (LCVD), and the like. Glazings having these advanced materials coated thereon are particularly useful in automotive and architectural applications which require reduced solar and infrared radiation transmittances.

Titanium nitride is a particularly useful advanced material having several desirable properties such as, for example, high melting point (2,950° C.), high hardness (8-9 on the Moh scale), excellent strength, high electrical conductivity, excellent solar and infrared reflectances, and nonreactivity with a variety of corrosive atmospheres. Furthermore, it is substantially unaffected by acids, excepting aqua regia; however, alkali compounds may cause its decomposition.

Conventional methods for preparing titanium nitride include the high temperature reaction of a source of titanium such as, for example, titanium tetrachloride with a source of nitrogen such as, for example, ammonia. Such a method is disclosed in U.S. Pat. No. 4,535,000 to Gordon. This chemical vapor deposition process has been used to form a film of titanium nitride on a ribbon of glass as it is being produced by the well-known float glass process.

It is known to prepare titanium nitride by the Pyrolysis of a polymeric precursor formed by reacting ammonia with a titanium dialkylamide. See Brown, G. M. and Maya, L., "Ammonolysis Products of the Dialkylamides of Titanium, Zirconium, and Niobium as Precursors to Metal Nitrides," Journal of the American Ceramic Society, v. 71 (1988) 78-82. Specifically, a titanium dialkylamide such as, for example, tetrakis(dimethylamido)titanium is reacted with liquid anhydrous ammonia to form an imido- or nitride-bridged polymeric precursor having the general formula $Ti_3(NX_2)(NH_2)_2N_3$, wherein X is an alkyl group. Thereafter, the precursor is pyrolyzed in an ammonia atmosphere to prepare titanium nitride. During the initial stages of the pyrolysis process, $NHX_2$ and $NH_3$ are released, forming a compound having the approximate composition $Ti_3N_4$. At a temperature of approximately 700° C. to 800° C., additional nitrogen is released thereby forming partially crystalline titanium nitride.

Also, it is known to prepare titanium nitride by the pyrolysis of a polymeric precursor formed by reacting tetrakis(dimethylamido)titanium with either liquid ammonia or a primary amine. See Seyferth, D. and Miganani, G., "The Preparation of Titanium Nitride and Titanium Carbonitride by the Preceramic Polymer Route," Gov. Rep. Announce. Index (US), v. 88 (1988) 827, 109. The publication discloses that tetrakis(dimethylamido)titanium is reacted with a primary amine such as n-butylamine to form a polymeric precursor which pyrolyzes under a stream of ammonia to give fairly Pure titanium nitride. Pyrolysis is carried out at a temperature of approximately 1,000° C.

Cowdell, R.T. and Fowles, G.W., "Amine Compounds of the Transition Metals. Part VI. The Reaction of Titanium (IV) Cloride with Some Aliphatic Amines," Journal of the Chemical Society (1960) 2522-2566, discloses a reaction between titanium tetrachloride and several primary amines. The article discloses that aminobasic titanium chlorides $TiCl_2(NHR)_2$ and their corresponding alkyl amine complexes $TiCl_2(NHR)_2,2NHR$ are formed. The article, however, does not suggest that such compounds may be utilized to form titanium nitride.

Finally, a recently allowed U.S. Pat. application, Ser. No. 07/625,180, discloses that a titanium tetrahalide may be reacted with at least one disilazane to prepare a titanium-containing metallo-organic precursor, which thereafter may be pyrolized to form bulk titanium nitride.

It would be desirable to prepare organometallic precursors to titanium nitride, which could be used as single-source precursors in a chemical vapor deposition process for forming a coating of titanium nitride on a substrate, or in a pyrolysis process to prepare bulk titanium nitride.

It must be noted that the prior art referred to hereinabove has been collected and examined only in light of the present invention as a guide. It is not to be inferred that such diverse art would otherwise be assembled absent the motivation provided by the present invention, nor that the cited prior art when considered in combination suggests the present invention absent the teachings herein.

SUMMARY OF THE INVENTION

Accordant with the present invention, a novel metallo-organic precursor to titanium nitride has surprisingly been discovered. The metallo-organic precursor generally characterized as a dimeric imido complex is a compound of the formula:

wherein R is a monovalent alkyl or aryl radical having from 1 to about 12 carbon atoms. Furthermore, the invention includes a process for preparing the novel metallo-organic precursor.

Also contemplated are processes for applying titanium nitride to the surface of a substrate by chemical vapor deposition. One embodiment of the process of the present invention utilizes the novel metallo-organic precursor as a starting material. The process includes the steps of:

A) heating a metal-organic precursor of the formula:

wherein R is a monovalent alkyl or aryl radical having from 1 to about 12 carbon atoms, to prepare a gaseous precursor; and B) directing the gaseous precursor against the surface of the substrate at a temperature sufficient to deposit a coating of titanium nitride thereon.

Another embodiment of the process of the present invention utilizes a titanium tetrahalide and a primary amine as starting materials. The process comprises the steps of:

A) contacting a titanium tetrahalide with a primary alkyl or aryl amine, to prepare an intermediate metallo-organic compound;

B) heating the intermediate metallo-organic compound to a temperature and for a period of time sufficient to prepare a metallo-organic precursor of the formula:

[Cl$_2$TiNR]$_2$, wherein R is a monovalent alkyl or aryl radical having from 1 to about 12 carbon atoms;

C) heating the metallo-organic precursor to prepare a gaseous precursor; and

D) directing the gaseous precursor against the surface of the substrate at a temperature sufficient to deposit a coating of titanium nitride thereon.

Finally, the present invention is useful for Preparing bulk titanium nitride by a process comprising the steps of:

A) contacting a titanium tetrahalide with a Primary alkyl or aryl amine, to prepare an intermediate metallo-organic compound;

B) heating the intermediate metallo-organic compound to a temperature and for a period of time sufficient to prepare a metallo-organic precursor of the formula:

[Cl$_2$TiNR]$_2$, wherein R is a monovalent alkyl or aryl radical having from 1 to about 12 carbon atoms; and C) heating the metallo-organic precursor to a temperature and at a pressure sufficient to pyrolyze the metallo-organic precursor.

The novel compositions and processes of the present invention are particularly well suited for preparing titanium nitride-coated solar control automotive and architectural glazings.

DETAILED DESCRIPTION OF THE PREFERRED EMBODIMENT

The present invention is directed to a novel metallo-organic precursor to titanium nitride for use in a chemical vapor deposition or pyrolysis process, and to its method of preparation. Additionally, the invention is directed to novel methods of applying a titanium nitride coating to the surface of a substrate by chemical vapor deposition, and a novel method for preparing bulk titanium nitride.

Chemical vapor deposition generally involves the formation of a metal, metal compound, or metal oxide coating on the surface of a heated substrate, by directing a gaseous precursor mixture against the surface which causes the gaseous precursor mixture to undergo a chemical reaction adjacent the surface to produce a coating thereon. Such coatings may be applied to the surface of a hot glass ribbon as it is being produced by the well-known float glass process, to produce infrared reflective solar control automotive and architectural glazings.

The present invention includes a metallo-organic Precursor which may be heated to form a gaseous precursor for use in a chemical vapor deposition process for the preparation of titanium nitride coatings. The metallo-organic precursor is a dimeric imido complex represented by the general formula:

[Cl$_2$TiNR]$_2$, wherein R is a monovalent alkyl or aryl radical having from 1 to about 12 carbon atoms. Examples of contemplated equivalent metallo-organic precursors having the same operability and utility include, but are not necessarily limited to, [Cl$_2$TiN(t-butyl)]$_2$, [Cl$_2$TiN(methyl)]$_2$, [Cl$_2$TiN(isopropyl)]$_2$, [Cl$_2$TiN(cyclohexyl)]$_2$, [Ci$_2$TiN(phenyl)]$_2$, and the like, as well as mixtures thereof. A preferred metallo-organic precursor, which may be heated to form a gaseous precursor to titanium nitride, is [Cl$_2$TiN(t-butyl)]$_2$ or tetrachlorodi-$\mu$-t-butylimidodititanium(IV).

The metallo-organic precursor of the present invention may be transformed into a gaseous precursor for the chemical vapor deposition of titanium nitride onto the surface of a substrate, by heating the metallo-organic precursor to a temperature from about 25° C. to about 500° C. At these temperatures, the metallo-organic precursor sublimes to form a gaseous precursor. Preferably, the temperature range is from about 100° C. to about 300° C. The step of heating the metallo-organic precursor is generally carried out at a pressure from about 10$^{-9}$ mm Hg to about 760 mm Hg. Preferably, the pressure is from about 0.01 mm Hg to about 0.1 mm Hg. These temperatures and pressures may vary over wide ranges, and are not sharply critical to the successful preparation of the gaseous precursor.

In a preferred embodiment of the process of the present invention, titanium nitride is deposited onto the surface of a ribbon of glass as it is being produced by the well-known float glass process. This process involves forming a glass substrate in the float tank, and continuously advancing the hot glass ribbon so produced past a treating station where the gaseous precursor may be directed against the surface of the glass. The gaseous precursor conveniently may be transported to the treating station by an inert carrier gas such as nitrogen. Such systems for conveying chemical vapor deposition reactant streams to the surface of a hot glass ribbon are well-known and do not form a part of the present invention.

Generally, the gaseous precursor is heated by contact with the hot surface of the substrate to be coated, thereby causing a chemical reaction which deposits a coating of titanium nitride thereon. This reaction is substantially instantaneous. The temperature for reaction of the gaseous precursor generally ranges from about 100° C. to about 2,000° C. Preferably, the temperature is from about 300° C. to about 700° C. Titanium nitride is easily deposited by this process at conventional soda-lime-silica glass processing temperatures, in which the temperature of the glass ranges from about 400° C. to about 700° C.

Metal nitride coatings may be deposited onto substrates by the process of the present invention at thicknesses from about 20 Angstroms to about 50,000 Angstroms. A preferred thickness range, suitable for preparing solar control automotive and architectural glazings, is from about 100 Angstroms to about 2,000 Angstroms. Such coatings may be deposited onto virtually any substrate that can withstand the reaction temperature, including, without limitation, glass, ceramic, quartz, metals, etc. A preferred substrate is a glass ribbon as it is being produced by a float glass facility. The glass may be of any thickness generally known in the industry as useful for making automotive or architectural glazings. A preferred coated glazing comprises glass having a film of titanium nitride deposited thereon.

Alternatively, the metallo-organic precursor of the present invention may be used to prepare bulk titanium nitride by pyrolysis. Thus, the metallo-organic Precursor is heated to a temperature from about 300° C. to about 1,000° C. at a pressure greater than about 760 mm Hg. Preferably, the temperature for pyrolysis is from about 400° C. to about 700° C. During this pyrolysis reaction, coordinated amine and other organics are released from the metallo-organic precursor. The time required for pyrolysis may range from a few minutes to several hours. As will be evident to those ordinarily skilled in the art, the temperatures, pressures, and periods of time required for the pyrolysis reaction may vary over wide limits, and are not sharply critical to the successful preparation of bulk titanium nitride.

The metallo-organic precursor of the present invention may be prepared by reacting a titanium tetrahalide with a primary alkyl or aryl amine, to prepare an intermediate metallo-organic compound, and thereafter heating the intermediate metallo-organic compound to a temperature and for a period of time sufficient to produce a metallo-organic precursor having the general formula:

$$[Cl_2TiNR]_2,$$

wherein R is a monovalent alkyl or aryl radical having from 1 to about 12 carbon atoms.

Titanium tetrahalides useful for preparing the metallo-organic precursor according to the present invention are well-known to those ordinarily skilled in the chemical art, and include $TiCl_4$, $TiBr_4$, and $TiI_4$. A preferred titanium tetrahalide is titanium tetrachloride, which may be produced by heating a quantity of titanium dioxide or a titanium-containing ore along with carbon while passing a stream of chlorine gas thereover. Details concerning the manufacture and characteristics of titanium tetrahalides are more fully set forth in Kirk-Othmer Concise Encyclopedia of Chemical Technology, John Wiley & Sons, NY (1985) pp. 1185-1186.

Primary alkyl and aryl amines useful for preparing the metallo-organic precursor according to the present invention are also well-known. Such primary amines are represented by the general formula:

$$NH_2R,$$

wherein R is a monovalent alkyl or aryl radical having from 1 to about 12 carbon atoms. Examples of contemplated equivalent primary amines having the same operability and utility include, but are not necessarily limited to, t-butylamine, methylamine, ethylamine, n-propylamine, isopropylamine, cyclohexylamine, aniline, naphthylamine, and the like, as well as mixtures thereof. A preferred primary amine is t-butylamine.

The titanium tetrahalide and primary alkyl or aryl amine are contacted together to form an intermediate metallo-organic compound believed to have the general formula:

$$Cl_2Ti(NHR)_2(NH_2R)_x,$$

wherein R is a monovalent alkyl or aryl radical having from 1 to about 12 carbon atoms and x is a value from 0 to 2. The titanium tetrahalide and primary alkyl or aryl amine may optionally be contacted in the present of a solvent such as, for example, dichloromethane, carbon tetrachloride, toluene, benzene, pentane, hexane, and the like, as well as mixtures thereof. A preferred solvent is dichloromethane. The solvent, if present, may comprise up to about 99% by weight of the reaction mixture. The titanium tetrahalide may be contacted with the primary alkyl or aryl amine in virtually any ratio, resulting in more or less efficient yields of product. Preferably, the titanium tetrahalide is contacted with at least about 6 stoichiometric equivalents of the primary amine. The reaction is generally carried out over a wide range of temperatures from about −100° C. to about 200° C. Preferably, the temperature is from about −80° C. to about 25° C.

The period of time required for the formation of the intermediate metallo-organic compound may vary over wide limits from several seconds to a few hours. It will be evident to one ordinarily skilled in the art that the temperatures, reaction times, and concentrations of reactants vary over wide limits and are not sharply critical to the successful preparation of the intermediate metallo-organic compound.

The intermediate metallo-organic compound is separated from the reaction mixture by means well-known to those ordinarily skilled in the chemical art, and further treated to form the metallo-organic precursor of the present invention represented by the general formula:

$$[Cl_2TiNR]_2,$$

wherein R is a monovalent alkyl or aryl radical having from 1 to about 12 carbon atoms. The intermediate metallo-organic compound is heated to a temperature and for a period of time sufficient to form the metallo-organic precursor. The intermediate metallo-organic compound may be heated to a temperature ranging over wide limits from about 100° C. to about 500° C., and for a period of time from about a few minutes to several days. Preferably, the temperature range is from about 180° C. to about 300° C. This heating step may be carried out at a pressure from about $10^{-9}$ mm Hg to about 760 mm Hg. Preferably, the pressure range is from about 0.01 mm Hg to about 0.1 mm Hg. During this heating step, coordinated amine and other organics are released from the intermediate metallo-organic compound. It will be recognized by those ordinarily skilled in the art that the temperatures, pressures, and reaction times for this heating step may vary over wide limits, and are not sharply critical to the successful preparation of the metallo-organic precursor of the present invention. The metallo-organic precursor prepared in this fashion may subsequently be utilized to deposit a coating of titanium nitride on a substrate by chemical vapor deposition, as described hereinabove.

EXAMPLE

Titanium tetrachloride is added to about six stoichiometric equivalents of t-butylamine in the presence of dichloromethane (about 90% by weight of the mixture) at about −78° C. under atmospheric pressure, and agitated for a period of about ¼ hour. The reaction produces an orange solid intermediate metallo-organic compound (yield about 85%) upon extraction with hexane.

The intermediate metallo-organic compound is heated to about 250° C. and maintained at a pressure of about $10^{-3}$ mm Hg for a period of about 2 hours, thereby producing the metallo-organic precursor $[Cl_2TiN(t\text{-butyl})]_2$. This material is observed to have a mass spectroscopy peak at about 380 atomic mass units, indicative of tetrachlorodi-μ-t-butylimidodititanium-(IV).

The metallo-organic precursor is heated to a temperature of about 250° C. at a pressure of about $10^{-3}$ mm Hg, thereby producing a gaseous precursor which is conveyed to the surface of a glass sheet maintained at a temperature of about 500° C. A gold-colored film of titanium nitride is deposited onto the surface of the glass sheet.

This example may be repeated with similar success by substituting the generically or specifically described reactants and/or reactant conditions recited herein for those used in the preceding Example. Thus, the isobutyl, 3-pentyl, isopropyl, and sec-butyl dimeric imido complexes have been prepared.

From the foregoing description, one ordinarily skilled in the art can easily ascertain the essential characteristics of this invention, and without departing from the spirit and scope thereof, can make various changes and modifications to the invention to adapt it to various usages and conditions.

What is claimed is:

1. A metallo-organic precursor of the formula:

$$[Cl_2TiNR]_2,$$

wherein R is a monovalent alkyl or aryl radical having from 1 to about 12 carbon atoms.

2. The metallo-organic precursor according to claim 1, wherein R is t-butyl.

3. A process for preparing a metallo-organic precursor, comprising the steps of:
A) contacting a titanium tetrahalide with a primary alkyl or aryl amine to prepare an intermediate metallo-organic compound; and
B) heating the intermediate metallo-organic compound to a temperature and for a period of time sufficient to prepare a compound of the formula:

$$[Cl_2TiNR]_2,$$

wherein R is a monovalent alkyl or aryl radical having from 1 to about 12 carbon atoms.

4. The process for preparing a metallo-organic precursor according to claim 3, wherein the titanium tetrahalide is titanium tetrachloride.

5. The process for preparing a metallo-organic precursor according to claim 3, wherein the primary amine is t-butylamine.

6. The process for preparing a metallo-organic precursor according to claim 3, wherein step A is conducted in the presence of a solvent.

7. The process for preparing a metallo-organic precursor according to claim 3, wherein the titanium tetrahalide is contacted with at least about 6 stoichiometric equivalents of the primary amine.

8. The process for preparing a metallo-organic precursor according to claim 3, wherein the titanium tetrahalide is contacted with the primary amine at a temperature from about −100° C. to about 200° C.

9. The process for preparing a metallo-organic precursor according to claim 3, wherein the intermediate metallo-organic compound is heated to a temperature from about 100° C. to about 500° C.

10. The process for preparing a metallo-organic precursor according to claim 3, wherein step B is carried out at a pressure from about $10^{-9}$ mm Hg to about 760 mm Hg.

11. A process for preparing a metallo-organic precursor, comprising the steps of:
A) contacting a titanium tetrahalide with at least about 6 stoichiometric equivalents of a primary alkyl or aryl amine, optionally in the presence of a solvent, at a temperature from about −80° C. to about 25° C., to prepare an intermediate metallo-organic compound; and
B) heating the intermediate metallo-organic compound to a temperature from about 180° C. to about 300° C., at a pressure from about 0.01 mm Hg to about 0.1 mm Hg, for a period of time sufficient to prepare a metallo-organic precursor of the formula:

$$[Cl_2TiNR]_2,$$

wherein R is a monovalent alkyl or aryl radical having from 1 to about 12 carbon atoms.

12. The process for preparing a metallo-organic precursor according to claim 11, wherein the titanium tetrahalide is titanium tetrachloride.

13. The process for preparing a metallo-organic precursor according to claim 11, wherein the primary amine is t-butylamine.

* * * * *